United States Patent
Kurita et al.

(10) Patent No.: US 9,427,212 B2
(45) Date of Patent: Aug. 30, 2016

(54) ULTRASONIC DIAGNOSTIC APPARATUS

(71) Applicant: Toshiba Medical Systems Corporation, Otawara-shi (JP)

(72) Inventors: Koichiro Kurita, Nasushiobara (JP); Jiro Higuchi, Otawara (JP); Osamu Nakajima, Otawara (JP); Takayuki Gunji, Otawara (JP); Itsuki Kuga, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 93 days.

(21) Appl. No.: 14/045,321

(22) Filed: Oct. 3, 2013

(65) Prior Publication Data

US 2014/0031687 A1 Jan. 30, 2014

Related U.S. Application Data

(63) Continuation of application No. PCT/JP2013/060657, filed on Apr. 8, 2013.

(30) Foreign Application Priority Data

Apr. 11, 2012 (JP) .................................. 2012-090409
Apr. 8, 2013 (JP) .................................. 2013-080561

(51) Int. Cl.
  *A61B 8/08* (2006.01)
  *A61B 8/14* (2006.01)
  *A61B 8/00* (2006.01)

(52) U.S. Cl.
  CPC ............ *A61B 8/5253* (2013.01); *A61B 8/145* (2013.01); *A61B 8/4254* (2013.01); *A61B 8/4483* (2013.01); *A61B 8/463* (2013.01); *A61B 8/466* (2013.01); *A61B 8/483* (2013.01); *A61B 8/54* (2013.01); *A61B 8/0883* (2013.01); *A61B 8/486* (2013.01); *A61B 8/488* (2013.01)

(58) Field of Classification Search
  CPC .. A61B 8/5253; A61B 8/0883; A61B 8/145; A61B 8/4254; A61B 8/4483; A61B 8/463; A61B 8/466; A61B 8/483; A61B 8/486; A61B 8/488; A61B 8/54
  See application file for complete search history.

(56) References Cited

U.S. PATENT DOCUMENTS

| 5,831,717 A * | 11/1998 | Ikebuchi ...................... 356/4.01 |
| 6,416,477 B1 * | 7/2002 | Jago .............................. 600/447 |
| 6,773,399 B2 * | 8/2004 | Xi et al. ........................ 600/443 |
| 2010/0099988 A1 | 4/2010 | Kurita et al. |
| 2010/0305441 A1 * | 12/2010 | Lin et al. ...................... 600/443 |
| 2011/0079083 A1 * | 4/2011 | Yoo et al. ........................ 73/632 |

FOREIGN PATENT DOCUMENTS

| JP | 2004-507298 A | 3/2004 |
| JP | 2011-217927 A | 11/2011 |
| WO | WO 02/16963 A2 | 2/2002 |

OTHER PUBLICATIONS

International Search Report mailed Jul. 2, 2013 for PCT/JP2013/060657 filed on Apr. 8, 2013 with English Translation of Categories.
International Written Opinion mailed Jul. 2, 2013 for PCT/JP2013/060657 filed on Apr. 8, 2013.

* cited by examiner

*Primary Examiner* — Michael Rozanski
(74) *Attorney, Agent, or Firm* — Oblon, McClelland, Maier & Neustadt, L.L.P.

(57) ABSTRACT

In an ultrasonic diagnostic apparatus according to an embodiment, a direction determining unit determines a moving direction of an ultrasonic probe. A scanning control unit controls a transmitting and receiving unit so as to repeatedly perform first scanning for acquiring first image data by transmitting and receiving an ultrasonic signal in a first direction and second scanning for acquiring second image data by transmitting and receiving the ultrasonic signal in a second direction inclined toward the moving direction with respect to the first direction. An image superimposing unit generates panoramic image data by superimposing a plurality of pieces of first image data acquired through the first scanning. A display control unit displays the second image data together with the panoramic image data or the first image data on a display unit during scanning.

9 Claims, 12 Drawing Sheets

ULTRASONIC DIAGNOSTIC APPARATUS

CROSS-REFERENCE TO RELATED APPLICATIONS

This application is a continuation of PCT international application Ser. No. PCT/JP2013/060657 filed on Apr. 8, 2013 which designates the United States, incorporated herein by reference, and which claims the benefit of priority from Japanese Patent Application No. 2012-090409, filed on Apr. 11, 2012, and No. 2013-080561, filed on Apr. 8, 2013, the entire contents of which are incorporated herein by reference.

FIELD

Embodiments described herein relate generally to an ultrasonic diagnostic apparatus.

BACKGROUND

Conventionally, a technology called panoramic scanning has been known as a technology related to ultrasonic diagnostic apparatuses. Panoramic scanning is a technology for obtaining image data of a wide area called panoramic image data by acquiring a plurality of pieces of image data while moving an ultrasonic probe along a body surface of a subject in a scanning direction and superimposing overlapping portions of the pieces of image data.

DETAILED DESCRIPTION

An ultrasonic diagnostic apparatus according to an embodiment includes an ultrasonic probe, a transmitting and receiving unit, a scanning control unit, an image superimposing unit, and a display control unit. The ultrasonic probe is configured to transmit and receive an ultrasonic signal to and from a subject. The transmitting and receiving unit is configured to drive the ultrasonic probe and scan the subject. The direction determining unit is configured to determine a moving direction of the ultrasonic probe. The scanning control unit is configured to control the transmitting and receiving unit so as to repeatedly perform first scanning for acquiring first image data by transmitting and receiving the ultrasonic signal in a first direction and second scanning for acquiring second image data by transmitting and receiving the ultrasonic signal in a second direction inclined toward the moving direction with respect to the first direction. The image superimposing unit is configured to generate panoramic image data by superimposing a plurality of pieces of first image data acquired through the first scanning. The display control unit is configured to display the second image data together with the panoramic image data or the first image data on a display unit during scanning.

Exemplary embodiments of an ultrasonic diagnostic apparatus are described below with reference to the accompanying drawings.

First Embodiment

Figure 1:
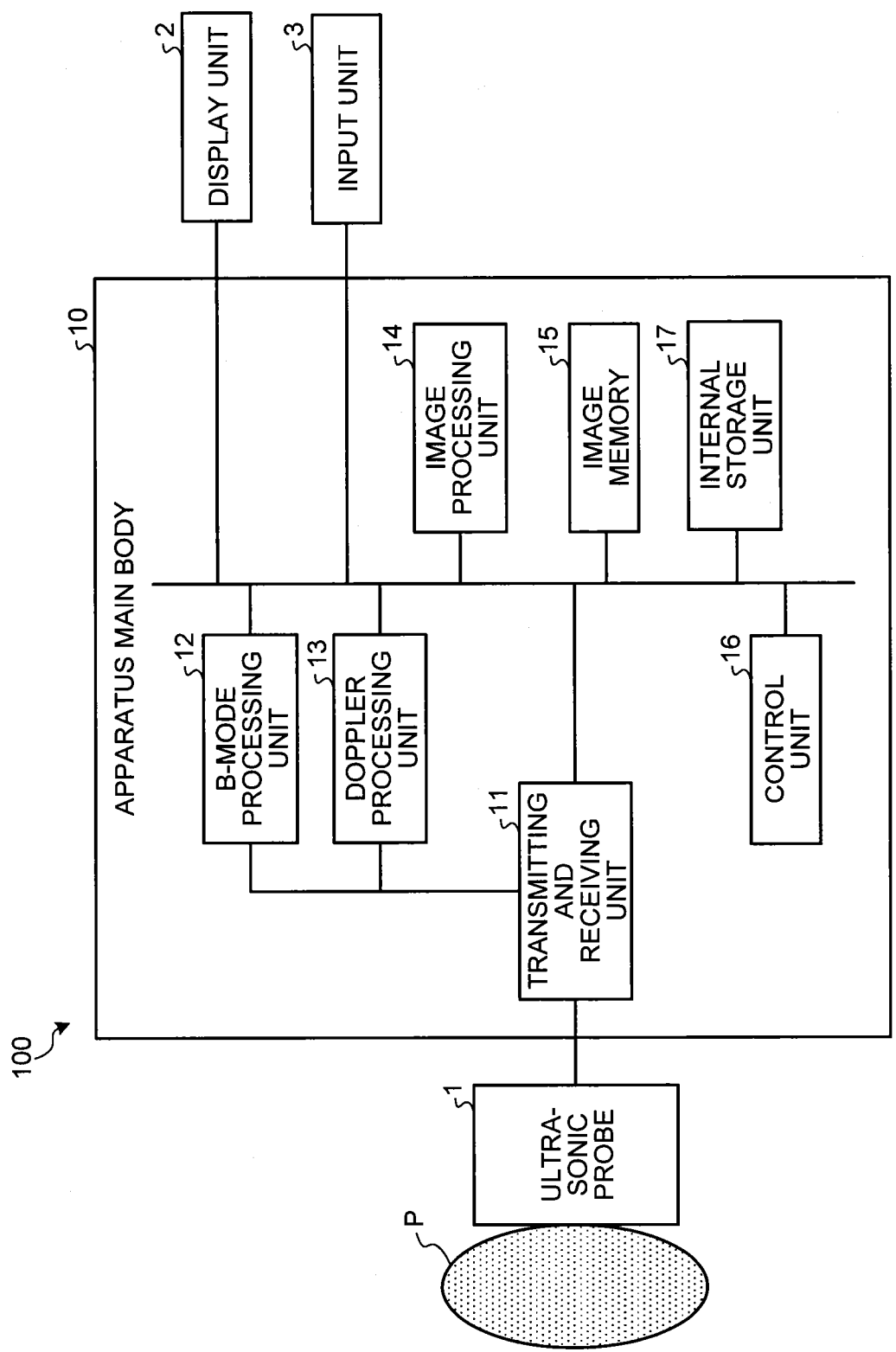
FIG. 1 is a functional block diagram of a configuration of an ultrasonic diagnostic apparatus according to a first embodiment.

FIG. 1 is a functional block diagram of a configuration of an ultrasonic diagnostic apparatus according to a first embodiment. As illustrated in FIG. 1, an ultrasonic diagnostic apparatus 100 according to the present embodiment includes an ultrasonic probe 1, a display unit 2, an input unit 3, and an apparatus main body 10. FIG. 1 is a functional block diagram and does not necessarily illustrate the hardware configuration.

The ultrasonic probe 1 includes a plurality of piezoelectric transducer elements. The piezoelectric transducer elements generate ultrasonic pulses based on a driving signal supplied from a transmitting and receiving unit 11, which will be described later, included in the apparatus main body 10. Furthermore, the piezoelectric transducer elements receive reflected waves from a subject P and convert the reflected waves into electrical signals. The ultrasonic probe 1 includes a matching layer provided to the piezoelectric transducer elements and a backing material that prevents ultrasound from propagating backward from the piezoelectric transducer elements.

If ultrasonic pulses are transmitted from the ultrasonic probe 1 to the subject P, the ultrasonic pulses thus transmitted are sequentially reflected by a discontinuity surface of acoustic impedance in a body tissue of the subject P. The ultrasonic pulses are then received by the piezoelectric transducer elements included in the ultrasonic probe 1 as echo signals. The amplitude of the echo signals thus received depends on difference in the acoustic impedance on the discontinuity surface by which the ultrasonic pulses are reflected. If the ultrasonic pulses thus transmitted are reflected by the surface of a moving bloodstream, a heart wall, or the like, the echo signals are subjected to a frequency shift depending on the velocity component of the moving body in the ultrasonic transmission direction because of the Doppler effect.

The display unit 2 is a monitor, for example. The display unit 2 displays a graphical user interface (GUI) used by an operator of the ultrasonic diagnostic apparatus 100 to input various types of instructions and setting requests with the input unit 3. The display unit 2 also displays an ultrasonic image and an analysis result generated by the apparatus main body 10.

The input unit 3 is a mouse, a keyboard, a button, a panel switch, a touch command screen, a foot switch, and a trackball, for example, and is connected to the apparatus main body 10. The input unit 3 receives various types of instructions and setting requests from the operator of the ultrasonic diagnostic apparatus 100 and transmits the various types of instructions and the setting requests thus received to the apparatus main body 10.

The apparatus main body 10 generates an ultrasonic image based on reflected waves received by the ultrasonic probe 1. As illustrated in FIG. 1, the apparatus main body 10 includes the transmitting and receiving unit 11, a B-mode processing unit 12, a Doppler processing unit 13, an image processing unit 14, an image memory 15, a control unit 16, and an internal storage unit 17.

The transmitting and receiving unit 11 includes a trigger generating circuit, a transmission delay circuit, and a pulsar circuit, for example, and supplies a driving signal to the ultrasonic probe 1. The pulsar circuit repeatedly generates a rate pulse for forming an ultrasonic pulse at a predetermined pulse repetition frequency (PRF). The PRF is also referred to as a rate frequency. The transmission delay circuit supplies each rate pulse generated by the pulsar circuit with a transmission delay time for each piezoelectric transducer element required to focus the ultrasonic pulses generated from the ultrasonic probe 1 into a beam and to determine transmission directivity. The trigger generating circuit applies a driving signal (a driving pulse) to the ultrasonic probe 1 at a timing based on the rate pulse. In other words, the transmission delay circuit changes the transmission delay time supplied to each rate pulse, thereby arbitrarily adjusting the transmission direction from the piezoelectric transducer element surface.

The transmitting and receiving unit 11 has a function of instantly changing a transmission frequency, a transmission drive voltage, and the like to perform a predetermined scanning sequence based on an instruction from the control unit 16, which will be described later. In particular, change of the transmission drive voltage is implemented by a linear amplifier transmission circuit that can instantly switch the value or a mechanism that electrically switches a plurality of power supply units.

The transmitting and receiving unit 11 includes an amplifier circuit, an analog/digital (A/D) converter, a reception delay circuit, an adder, and an orthogonal detection circuit. The transmitting and receiving unit 11 performs various types of processing on a reflected wave signal received by the ultrasonic probe 1 to generate reflected wave data. The amplifier circuit amplifies the reflected wave signal for each channel to perform gain correction processing. The A/D converter performs A/D conversion on the reflected wave signal on which the gain correction is performed. The reception delay circuit supplies a reception delay time required to determine reception directivity to digital data. The adder performs addition processing of the reflected wave signal to which the reception delay time is supplied by the reception delay circuit. The addition processing performed by the adder emphasizes a reflection component in a direction corresponding to the reception directivity of the reflected wave signal.

The B-mode processing unit 12 receives reflected wave data from the transmitting and receiving unit 11. The B-mode processing unit 12 then performs logarithmic amplification, envelope detection processing, and the like on the reflected wave data to generate data (B-mode data) in which a signal intensity is represented by a luminance level. The B-mode processing unit 12 also generates M-mode data, which will be described later.

The Doppler processing unit 13 performs a frequency analysis on velocity information of the reflected wave data received from the transmitting and receiving unit 11 to extract a bloodstream, a tissue, and a contrast medium echo component by the Doppler effect. The Doppler processing unit 13 then generates data (Doppler data) by extracting moving body information, such as an average velocity, dispersion, and power, at multiple points.

The image processing unit 14 generates an ultrasonic image from the B-mode data and the M-mode data generated by the B-mode processing unit 12 and the Doppler data generated by the Doppler processing unit 13. Specifically, the image processing unit 14 generates a B-mode image from the B-mode data, an M-mode image from the M-mode data, and a Doppler image from the Doppler data. Furthermore, the image processing unit 14 performs coordinate conversion, data interpolation, or the like, thereby converting (scan-converting) a scanning line signal string in ultrasonic scanning into a scanning line signal string in a video format typified by television, for example. Thus, the image processing unit 14 generates the ultrasonic image (the B-mode image, the M-mode image, and the Doppler image) as a display image.

The image memory 15 is a memory that stores therein an ultrasonic image generated by the image processing unit 14 and an image generated by processing the ultrasonic image. After a diagnosis, for example, the operator can retrieve an image stored during an examination, and the image can be reproduced as a still image or a moving image using a plurality of images. Furthermore, the image memory 15 stores therein an image luminance signal that passes through the transmitting and receiving unit 11, other pieces of raw data, and image data acquired via a network, for example, as needed.

The control unit 16 controls the whole processing in the ultrasonic diagnostic apparatus 100. Specifically, the control unit 16 controls processing of the transmitting and receiving unit 11, the B-mode processing unit 12, the Doppler processing unit 13, and the image processing unit 14 and performs control such that the ultrasonic image and the like stored in the image memory 15 are displayed on the display unit 2 based on various types of instructions and setting requests input by the operator through the input unit 3 and on various types of computer programs and various types of setting information read from the internal storage unit 17.

The internal storage unit 17 stores therein an apparatus control program for performing transmission and reception of ultrasound, image processing, and display processing, and various types of data, such as diagnostic information (e.g., a patient ID and an opinion of a doctor), a diagnostic protocol, and various types of setting information. The internal storage unit 17 is also used to retain an image stored in the image memory 15 as needed, for example.

The transmitting and receiving unit 11 and other units included in the apparatus main body 10 may be configured as hardware, such as an integrated circuit, or may be configured as a computer program modularized as software.

With such a configuration, the ultrasonic diagnostic apparatus 100 according to the present embodiment has a function to perform panoramic scanning. In the description below, after explanation of conventional panoramic scanning, the panoramic scanning performed by the ultrasonic diagnostic apparatus 100 according to the present embodiment is described.

Figure 2:
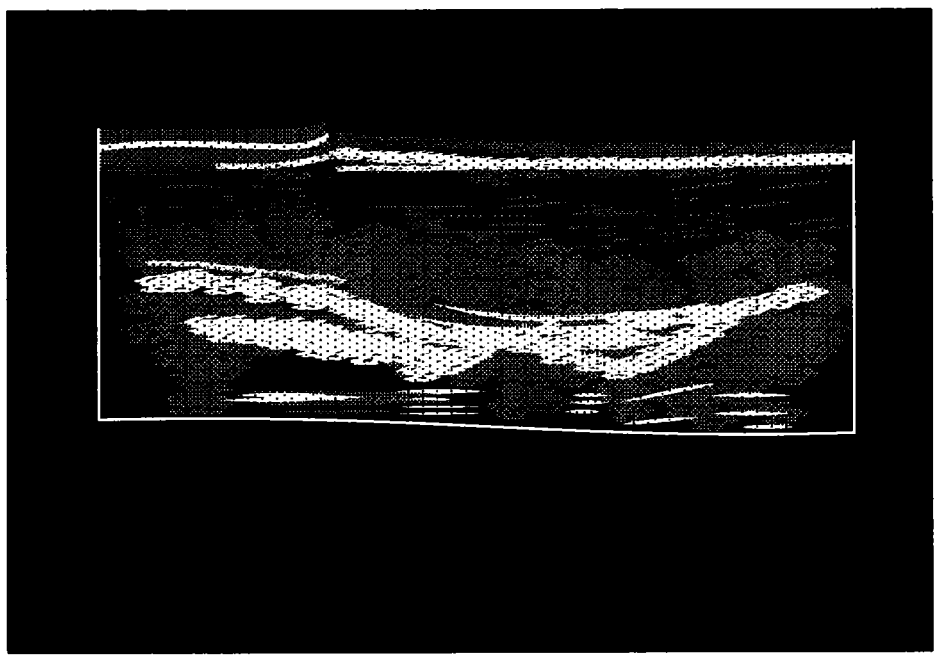
FIG. 2 is a view of panoramic image data obtained by conventional panoramic scanning.

FIG. 2 is a view of panoramic image data obtained by the conventional panoramic scanning. As illustrated in FIG. 2, in the panoramic scanning, a plurality of pieces of image data are acquired while an ultrasonic probe is being moved along a body surface of a subject in a scanning direction, and overlapping portions of the pieces of image data are superimposed. Thus, image data of a wide area called panoramic image data is obtained.

Figure 3:
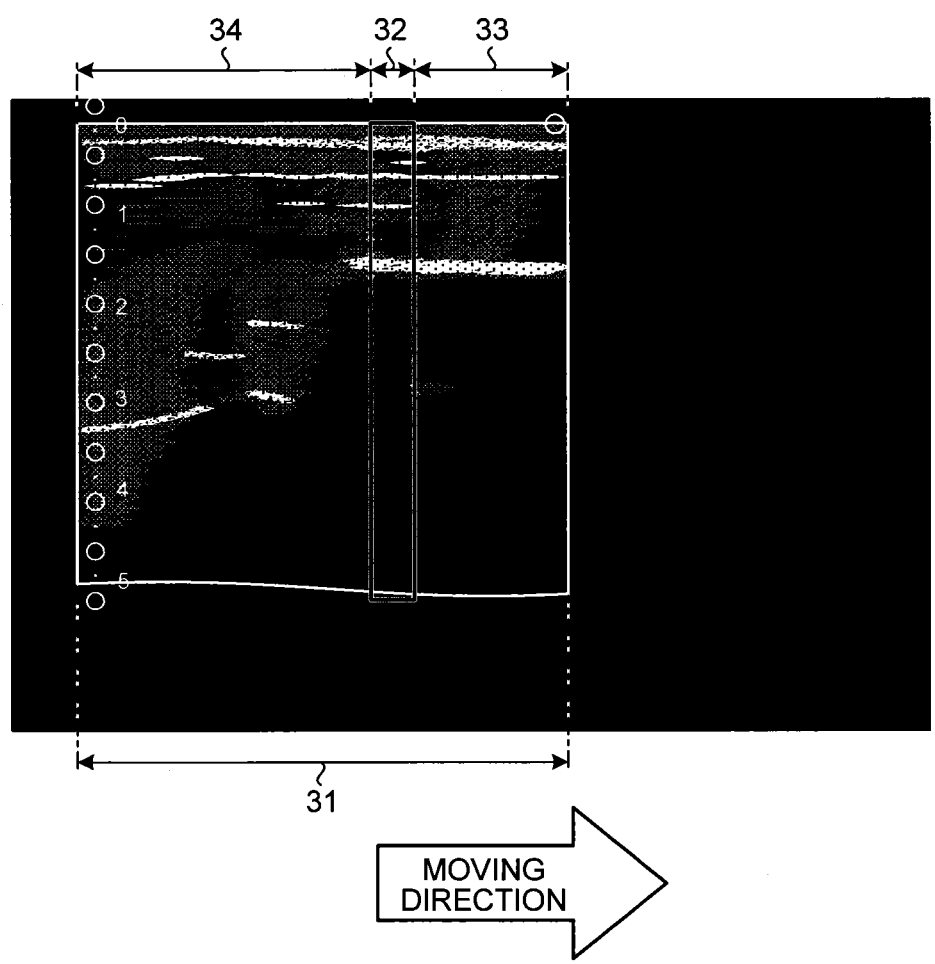
FIG. 3 is a view for explaining generation and display of panoramic image data in the conventional panoramic scanning.

FIG. 3 is a view for explaining generation and display of panoramic image data in the conventional panoramic scanning. As illustrated in FIG. 3, in the conventional panoramic scanning, a superimposing area 32 is set in a range 31 that can be scanned by the ultrasonic probe. The superimposing area 32 is an area used as a range for superimposing image data. The size of the area is set depending on computing capacity of the apparatus, for example. Furthermore, in the panoramic scanning, scanning for transmitting and receiving ultrasonic signals in the depth direction of the subject is repeatedly performed, thereby continuously acquiring a plurality of pieces of image data along with movement of the ultrasonic probe. Every time image data is acquired, a portion corresponding to the superimposing area 32 in the image data is superimposed with an overlapping portion in image data acquired previously, whereby panoramic image data is generated.

As illustrated in FIG. 3, the panoramic image data thus generated is displayed on a display unit during scanning in the panoramic scanning. At this time, image data is displayed as a live image in a range 33 positioned before the superimposing area 32 in a moving direction of the ultrasonic probe in the range 31 that can be scanned by the ultrasonic probe. By contrast, superimposed image data is continuously displayed as a still image in a range 34 positioned after the superimposing area 32 in the moving direction of the ultrasonic probe. Thus, an operator moves the ultrasonic probe while observing the state of the image data displayed as a live image.

In the conventional panoramic scanning, however, the range 33 displayed as a live image is only a part of the range 31 that can be scanned by the ultrasonic probe as illustrated in FIG. 3, for example. Thus, the field of view viewable by the operator in the moving direction of the ultrasonic probe is made narrow. As a result, when the operator moves the ultrasonic probe, the operator may possibly fail to notice presence of an object that causes an artifact, such as a curvature of the body and a bone, in time. If the operator moves the ultrasonic probe without noticing the presence of the object that causes an artifact, the panoramic image data may possibly show a result unintended by the operator. As a result, it may possibly be necessary to redo the scanning.

To address such a problem, in the panoramic scanning, the field of view in the moving direction of the ultrasonic probe may be expanded. In the conventional technology, for example, to expand the field of view in the scanning direction, trapezoidal scanning or oblique scanning (inclined scanning) may be performed.

Figure 4:
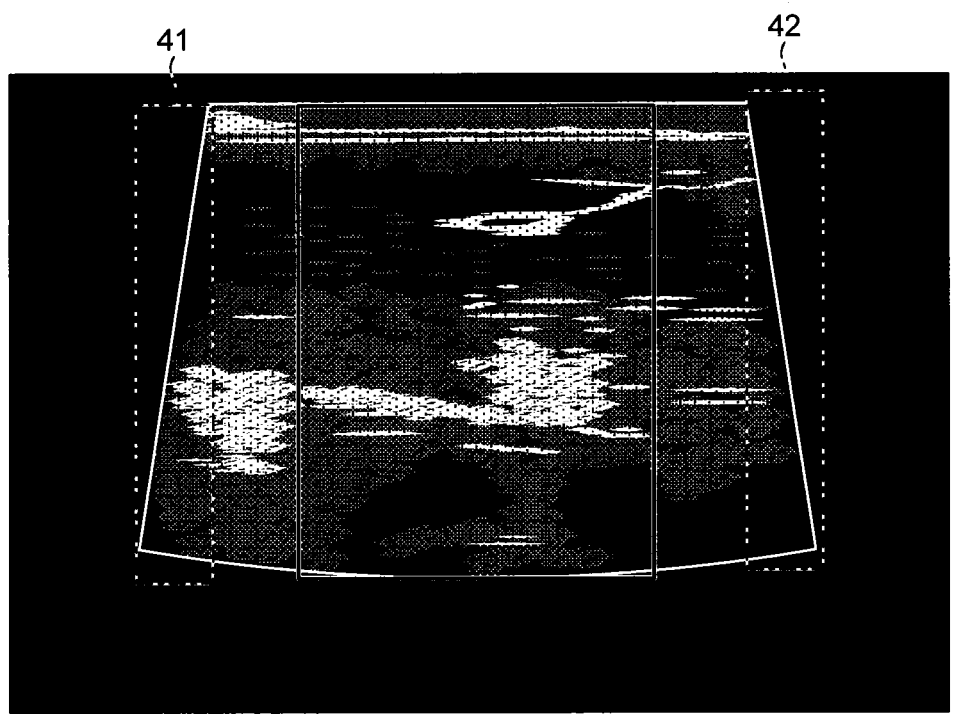
FIG. 4 is a view for explaining conventional trapezoidal scanning.

FIG. 4 is a view for explaining conventional trapezoidal scanning. As illustrated in FIG. 4, the trapezoidal scanning is scanning for transmitting and receiving ultrasonic signals obliquely with respect to the depth direction in the whole scanning range or both ends thereof such that both ends of image data to be acquired extend radially. With the trapezoidal scanning, it is possible to expand the field of view in the scanning direction correspondingly to the radially extended portions on both the ends of the image data (refer to a range 41 and a range 42 illustrated in FIG. 4) compared with the scanning for transmitting and receiving ultrasonic signals only in the depth direction.

Figure 5:
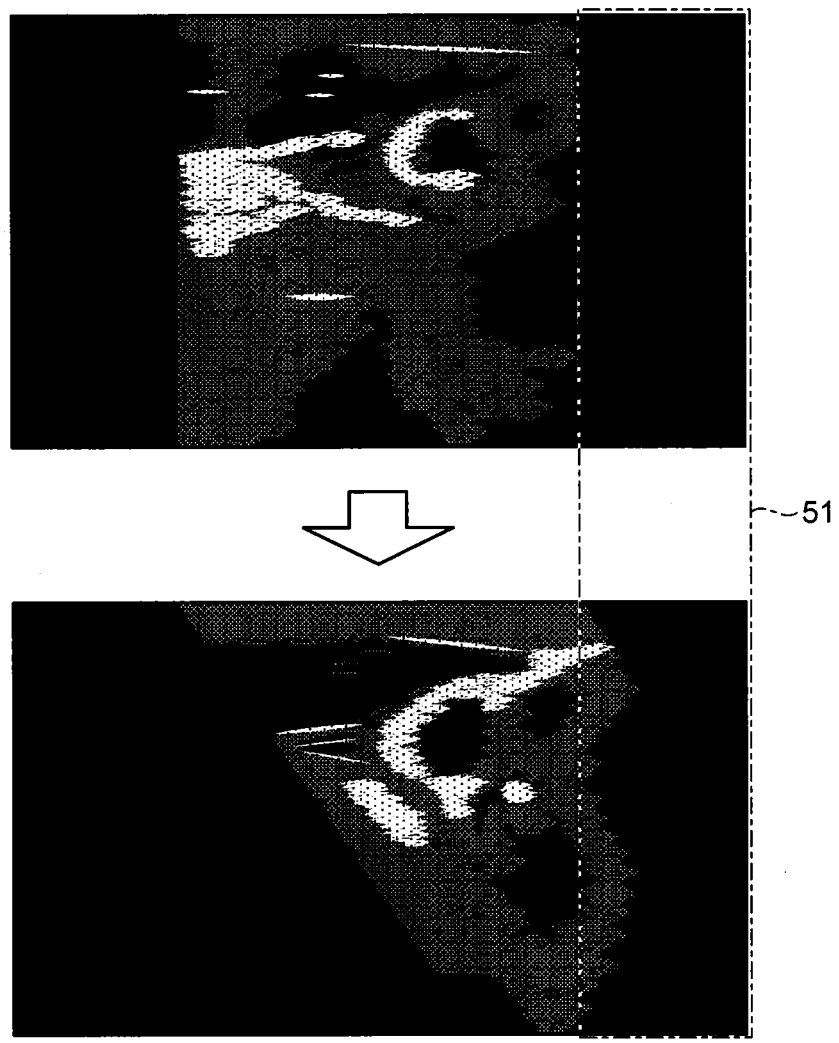
FIG. 5 is a view for explaining conventional oblique scanning.

FIG. 5 is a view for explaining conventional oblique scanning. As illustrated in FIG. 5, the oblique scanning is scanning for transmitting and receiving ultrasonic signals in a direction inclined toward the scanning direction with respect to the depth direction of the subject (refer to the lower figure in FIG. 5). With the oblique scanning, ultrasonic signals are transmitted and received in the direction inclined toward the scanning direction with respect to the depth direction. Thus, it is possible to expand the field of view in the scanning direction compared with the scanning for transmitting and receiving ultrasonic signals only in the depth direction (refer to a range 51 illustrated in FIG. 5).

In both the conventional trapezoidal scanning and oblique scanning, however, the ultrasonic signals are transmitted and received in a direction inclined with respect to the depth direction. As a result, grating lobe may possibly occur, thereby reducing image quality of the image data. For this reason, it is conventionally difficult to use the trapezoidal scanning and the oblique scanning for the purpose of expanding the field of view in the moving direction of the ultrasonic probe.

By contrast with the conventional technology, the ultrasonic diagnostic apparatus 100 according to the present embodiment determines the moving direction of the ultrasonic probe. The ultrasonic diagnostic apparatus 100 then repeatedly performs first scanning for acquiring first image data by transmitting and receiving ultrasonic signals in a first direction and second scanning for acquiring second image data by transmitting and receiving ultrasonic signals in a second direction inclined toward the moving direction of the ultrasonic probe with respect to the first direction. Subsequently, the ultrasonic diagnostic apparatus 100 generates panoramic image data by superimposing a plurality of pieces of first image data acquired through the first scanning. During the scanning, the ultrasonic diagnostic apparatus 100 displays the second image data together with the panoramic image data or the first image data on the display unit 2.

While an explanation will be made of the case where the first direction in the first scanning corresponds to the depth direction of the subject (direction perpendicular to the subject) in the present embodiment, the embodiments are not limited thereto. Assuming that an angle representing an inclination with respect to the depth direction of the subject is an oblique angle, for example, the relation between an oblique angle θ1 of the first direction in the first scanning and an oblique angle θ2 of the second direction in the second scanning simply needs to satisfy θ1<θ2. The first direction may satisfy θ1<0, that is, the first direction may be inclined toward a direction opposite to the moving direction of the ultrasonic probe, for example. At this time, by selecting an optimum angle for the tissue structure of the subject as the oblique angle of the first direction in the first scanning, it is possible to improve the image quality of the panoramic image to be obtained. By adjusting the oblique angle such that the oblique angle is perpendicular to the structure in the subject and transmitting ultrasonic signals, for example, intense reflected signals can be obtained.

In other words, the ultrasonic diagnostic apparatus 100 according to the present embodiment transmits and receives ultrasonic signals in a direction inclined toward the moving direction of the ultrasonic probe with respect to the depth direction of the subject during scanning in the panoramic scanning to acquire the second image data. The ultrasonic diagnostic apparatus 100 then displays the second image data together with the panoramic image data. The ultrasonic diagnostic apparatus 100 according to the present embodiment displays the second image data, thereby expanding the field of view in the moving direction of the ultrasonic probe. The ultrasonic diagnostic apparatus 100 according to the present embodiment will be specifically described below.

Figure 6:
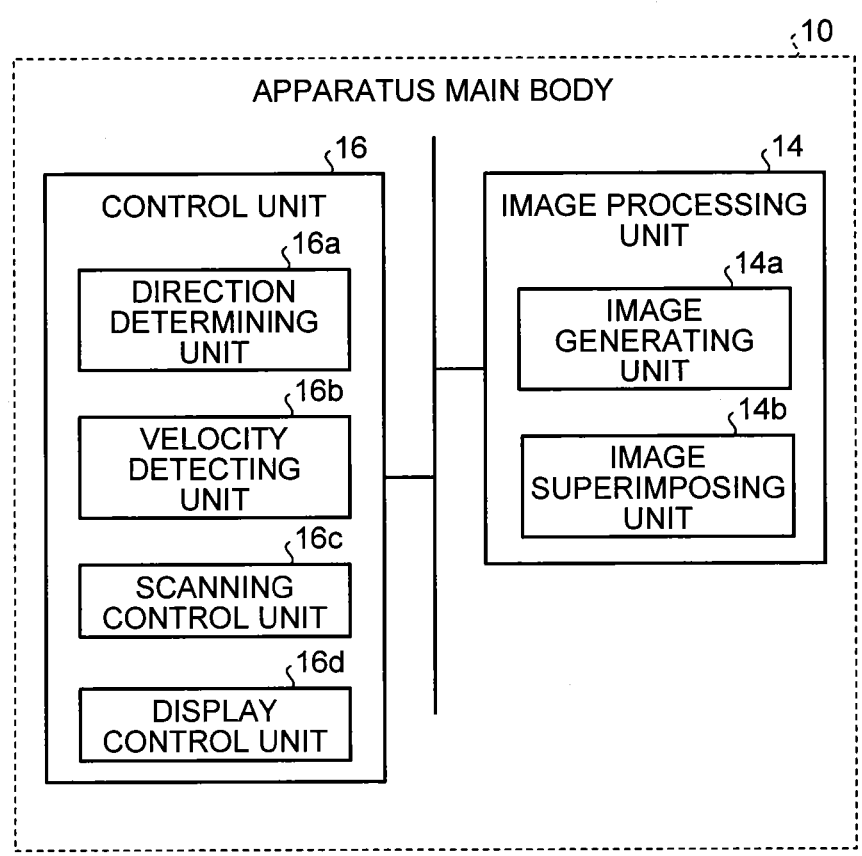
FIG. 6 is a functional block diagram of a detailed configuration of the ultrasonic diagnostic apparatus according to the first embodiment.

FIG. 6 is a functional block diagram of a detailed configuration of the ultrasonic diagnostic apparatus 100 according to the first embodiment. FIG. 6 illustrates the configurations of the control unit 16 and the image processing unit 14 among the units illustrated in FIG. 1. FIG. 6 is a functional block diagram and does not necessarily illustrate the hardware configuration.

As illustrated in FIG. 6, the image processing unit 14 includes an image generating unit 14a and an image superimposing unit 14b. The control unit 16 includes a direction determining unit 16a, a velocity detecting unit 16b, a scanning control unit 16c, and a display control unit 16d.

The direction determining unit 16a determines the moving direction of the ultrasonic probe 1. Specifically, the direction determining unit 16a detects the moving direction of the ultrasonic probe 1 based on the pieces of first image data continuously acquired along with the movement of the ultrasonic probe 1 while the panoramic scanning is being performed. When an overlapping portion of two pieces of temporally consecutive first image data is specified by pattern matching performed by the image superimposing unit 14b, which will be described later, for example, the direction determining unit 16a determines the moving direction of the ultrasonic probe 1 based on a directional vector indicating a positional relation between the pieces of first image data. If no moving direction of the ultrasonic probe 1 is detected, the direction determining unit 16a determines that the ultrasonic probe 1 is not moving. The direction determining unit 16a may detect the moving direction of the ultrasonic probe 1 with a position sensor attached to the ultrasonic probe 1, for example.

The velocity detecting unit 16b detects the velocity of movement of the ultrasonic probe 1. The velocity detecting unit 16b, for example, detects the velocity of movement of the ultrasonic probe 1 based on the pieces of first image data continuously acquired along with the movement of the ultrasonic probe 1 while the panoramic scanning is being performed. When an overlapping portion of two pieces of temporally consecutive first image data is specified by pattern matching performed by the image superimposing unit 14b, which will be described later, for example, the velocity detecting unit 16b calculates the velocity of movement of the ultrasonic probe 1 based on the magnitude of a directional vector indicating a positional relation between the pieces of first image data and on a time interval of acquisition of the first image data. The velocity detecting unit 16b may detect the moving velocity of the ultrasonic probe 1 with the position sensor attached to the ultrasonic probe 1, for example.

The scanning control unit 16c controls scanning performed by the transmitting and receiving unit 11 based on the moving direction of the ultrasonic probe 1 determined by the direction determining unit 16a and the velocity of the ultrasonic probe 1 detected by the velocity detecting unit 16b.

Specifically, the scanning control unit 16c controls the transmitting and receiving unit 11 so as to repeatedly perform the first scanning for acquiring the first image data by transmitting and receiving ultrasonic signals in the depth direction of the subject and the second scanning for acquiring the second image data by transmitting and receiving ultrasonic signals in a direction inclined toward the moving direction with respect to the depth direction of the subject. While the ultrasonic probe 1 is being moved, the scanning control unit 16c controls the transmitting and receiving unit 11 so as to stop scanning in the range positioned after the superimposing area in the moving direction of the ultrasonic probe 1 in the range that can be scanned by the ultrasonic probe 1 in the first scanning.

Figure 7:
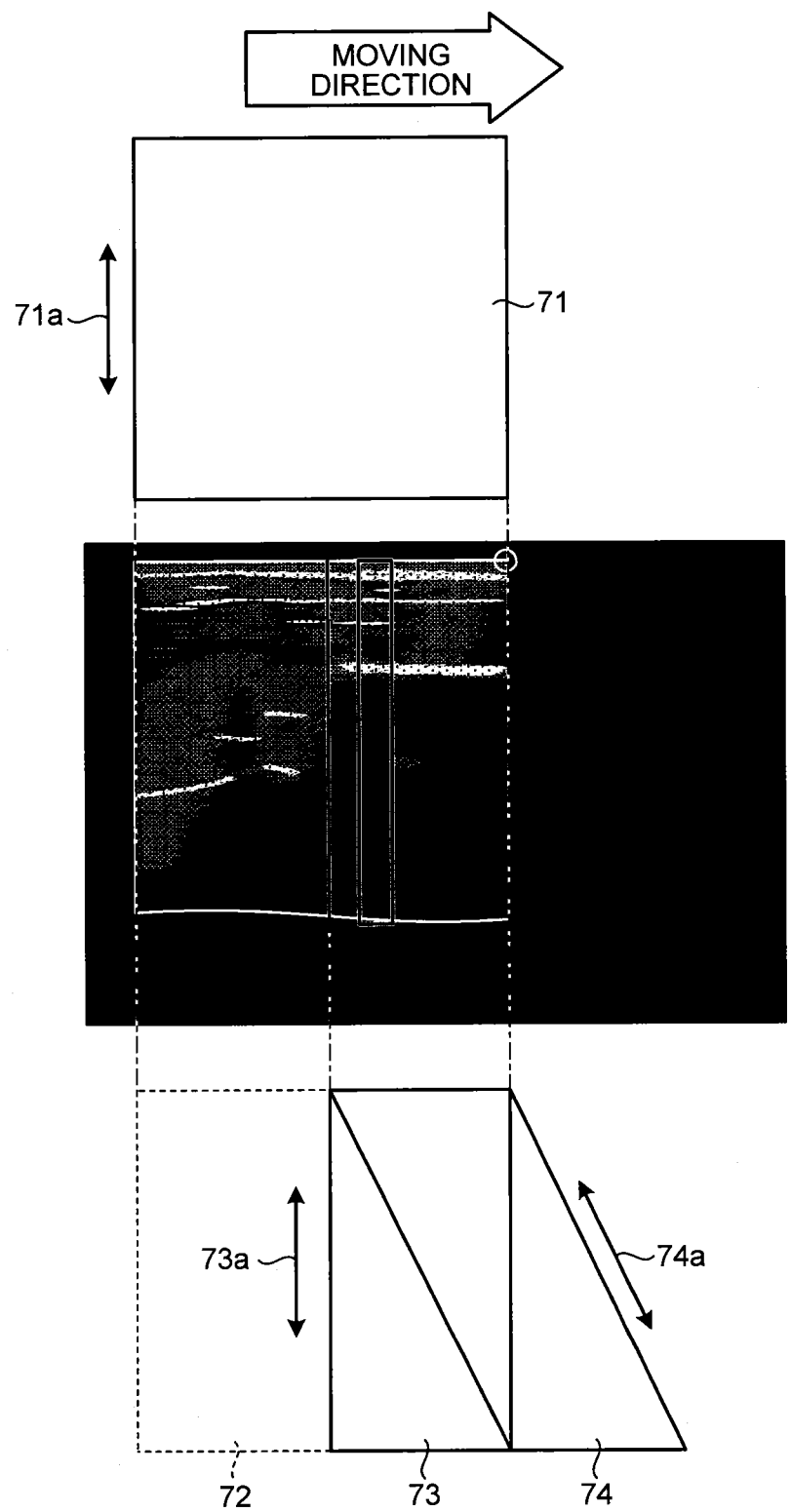
FIG. 7 is a view of scanning control performed by a scanning control unit according to the first embodiment.

FIG. 7 is a view of scanning control performed by the scanning control unit 16c according to the first embodiment. As illustrated in the upper figure of FIG. 7, when the direction determining unit 16a determines that the ultrasonic probe 1 is not being moved, the scanning control unit 16c performs scanning for transmitting and receiving ultrasonic signals in the depth direction of the subject (direction of an arrow 71a) on a range 71 that can be scanned by the ultrasonic probe.

If the direction determining unit 16a determines the moving direction of the ultrasonic probe 1, the scanning control unit 16c controls the transmitting and receiving unit 11 so as to perform the first scanning for acquiring the first image data by transmitting and receiving ultrasonic signals in the depth direction of the subject as illustrated in the lower figure of FIG. 7. At this time, the scanning control unit 16c controls the transmitting and receiving unit 11 so as to stop scanning in a range 72 positioned after the superimposing area in the moving direction of the ultrasonic probe 1 in the range 71 that can be scanned by the ultrasonic probe 1. In other words, the scanning control unit 16c controls the transmitting and receiving unit 11 so as to perform scanning in the depth direction of the subject (direction of an arrow 73a) only on a range 73 positioned before the range 72 in the moving direction of the ultrasonic probe 1 as the first scanning.

As described above, because the scanning control unit 16c stops scanning in the range positioned after the superimposing area in the moving direction of the ultrasonic probe 1, no scanning is performed on a range not to be used for superimposing the panoramic image data. Thus, it is possible to eliminate unnecessary scanning while the panoramic scanning is being performed.

Furthermore, if the direction determining unit 16a determines the moving direction of the ultrasonic probe 1, the scanning control unit 16c controls the transmitting and receiving unit 11 so as to perform the second scanning for acquiring the second image data by transmitting and receiving ultrasonic signals in a direction inclined toward the moving direction with respect to the depth direction of the subject as illustrated in the lower figure of FIG. 7. In other words, the scanning control unit 16c controls the transmitting and receiving unit 11 so as to perform scanning in the direction (direction of an arrow 74a) inclined toward the moving direction with respect to the depth direction of the subject on a range 74 expanded obliquely toward the moving direction with respect to the depth direction of the subject as the second scanning.

As described above, the scanning control unit 16c performs the second scanning by transmitting and receiving ultrasonic signals in a direction inclined toward the moving direction determined by the direction determining unit 16a. Thus, it is possible to automatically expand the field of view in the moving direction correspondingly to the direction in which the ultrasonic probe 1 is moved by the operator. As a result, compared with the case where the direction in which the field of view is expanded is fixed to one of the scanning directions like in the conventional oblique scanning, it is possible to increase the usability of the apparatus.

While the ultrasonic probe 1 is being moved, the scanning control unit 16c controls the transmitting and receiving unit 11 such that the number of beams output in the second scanning is smaller than the number of beams output to the range in which the scanning is stopped in the first scanning. As described above, the scanning control unit 16c performs control such that the second scanning is performed with a smaller number of beams than the number of beams for the range in which the scanning is stopped, thereby making it possible to increase the frame rate while the ultrasonic probe 1 is being moved. As a result, it is possible to improve the image quality of the image data displayed as a live image.

Furthermore, the scanning control unit 16c controls the transmitting and receiving unit 11 so as to change the second direction depending on the velocity of movement of the ultrasonic probe 1. Specifically, the scanning control unit 16c controls the transmitting and receiving unit 11 so as to change the angle of the direction of transmitting and receiving ultrasonic signals in the second scanning depending on the velocity of movement of the ultrasonic probe 1. At this time, based on the velocity of the ultrasonic probe 1 detected by the velocity detecting unit 16b, the scanning control unit 16c calculates the angle in the second scanning such that the angle with respect to the depth direction of the subject increases as the velocity of the ultrasonic probe 1 increases.

Figure 8:
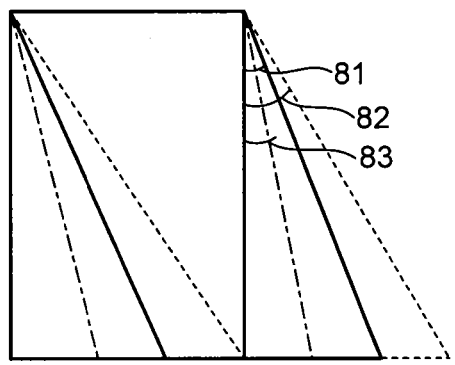
FIG. 8 is a view of control of an angle in second scanning performed by the scanning control unit according to the first embodiment.

FIG. 8 is a view of control of the angle in the second scanning performed by the scanning control unit 16c according to the first embodiment. As illustrated in FIG. 8, for example, an assumption is made that the scanning control unit 16c performs the second scanning at an angle 81 with respect to the depth direction at a first point. If the velocity of the ultrasonic probe 1 detected by the velocity detecting unit 16b at a second point posterior to the first point is higher than that at the first point, the scanning control unit 16c controls the transmitting and receiving unit 11 so as to perform the second scanning at an angle 82 larger than the angle 81. By contrast, if the velocity of the ultrasonic probe 1 detected by the velocity detecting unit 16b at the second point posterior to the first point is lower than that at the first point, the scanning control unit 16c controls the transmitting and receiving unit 11 so as to perform the second scanning at an angle 83 smaller than the angle 81.

As described above, the scanning control unit 16c changes the angle of the direction of transmitting and receiving ultrasonic signals in the second scanning depending on the velocity of the ultrasonic probe 1. When the operator moves the ultrasonic probe 1 at a higher velocity, the field of view in the moving direction can be expanded. As a result, it is possible to increase the visibility in the moving direction of the ultrasonic probe. By contrast, when the operator moves the ultrasonic probe 1 at a lower velocity, the angle in the second scanning can be made smaller. As a result, it is possible to reduce occurrence of grating lobe, thereby improving the image quality of the second image data.

The scanning control unit 16c controls the transmission delay time for each of the piezoelectric transducer elements included in the ultrasonic probe 1, thereby controlling the inclinations of the first direction and the second direction. Specifically, the scanning control unit 16c changes the transmission delay time supplied to each rate pulse by the transmission delay circuit of the transmitting and receiving unit 11, thereby changing the first direction and the second direction.

The image generating unit 14a generates image data for display from the B-mode data generated by the B-mode processing unit 12. Specifically, the image generating unit 14a performs coordinate conversion, data interpolation, or the like on the B-mode data generated by the B-mode processing unit 12, thereby generating image data for displaying a B-mode image. In the present embodiment, the image generating unit 14a generates the first image data from B-mode data acquired through the first scanning and the second image data from B-mode data acquired through the second scanning.

The image superimposing unit 14b generates panoramic image data by superimposing overlapping portions of the pieces of first image data continuously acquired along with the movement of the ultrasonic probe 1. Specifically, every time first image data is acquired, the image superimposing unit 14b superimposes a portion corresponding to the superimposing area set in a part of the range that can be scanned by the ultrasonic probe 1 in the first image data thus acquired, with an overlapping portion in first image data generated previously, thereby generating the panoramic image data.

The image superimposing unit 14b generates the panoramic image data in a method similar to that in the conventional panoramic scanning explained with reference to FIGS. 2 and 3. The image superimposing unit 14b, for example, uses a typical pattern matching technology, such as a sum of absolute difference (SAD) method, to perform superimposing processing for superimposing the overlapping portions in the image data. The image superimposing unit 14b according to the present embodiment uses no second image data generated by the image generating unit 14a, that is, no image data in an oblique direction for generation of the panoramic image data. As a result, the image quality of the panoramic image data is not reduced.

Figure 9:
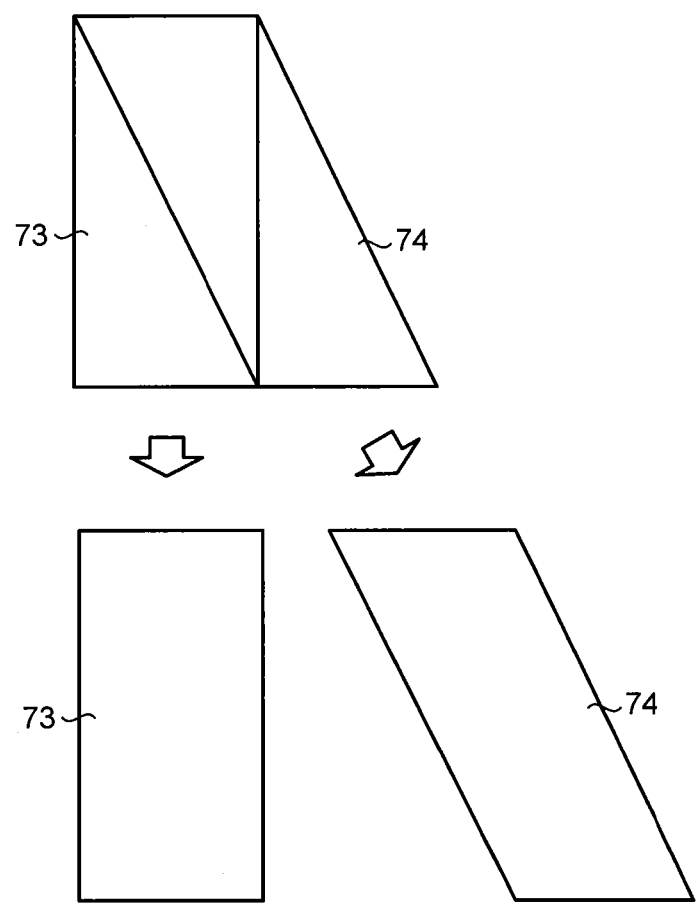
FIG. 9 is a view of generation of panoramic image data carried out by an image superimposing unit according to the first embodiment.

FIG. 9 is a view of generation of panoramic image data carried out by the image superimposing unit 14b according to the first embodiment. As illustrated in FIG. 9, for example, the image superimposing unit 14b uses only the first image data acquired through the scanning of the range 73 among the range 73 and the range 74 illustrated in the lower figure of FIG. 7 for generation of the panoramic image data. By contrast, the second image data acquired through the scanning of the range 74 is not used for superimposing of the panoramic image data. The second image data is displayed on the display unit 2 as information indicating the state in the travelling direction of the ultrasonic probe 1 by the display control unit 16d, which will be described later.

The display control unit 16d displays the second image data together with the panoramic image data on the display unit 2 during the scanning. Specifically, while the panoramic scanning is being performed, the display control unit 16d displays the panoramic image data generated by the image superimposing unit 14b and the second image data generated by the image generating unit 14a in a superimposed manner on the display unit 2 as illustrated in the lower figure of FIG. 7. Thus, it is possible to expand the field of view in the travelling direction of the ultrasonic probe 1 by displaying the second image data while the panoramic scanning is being performed.

The panoramic image data displayed during the scanning may be a part of image data extending in the lateral direction along with superimposing the image data. Alternatively, the display control unit 16d may display the second image data together with the first image data on the display unit 2 during the scanning. The first image data is displayed as a live image during the scanning.

Figure 10:
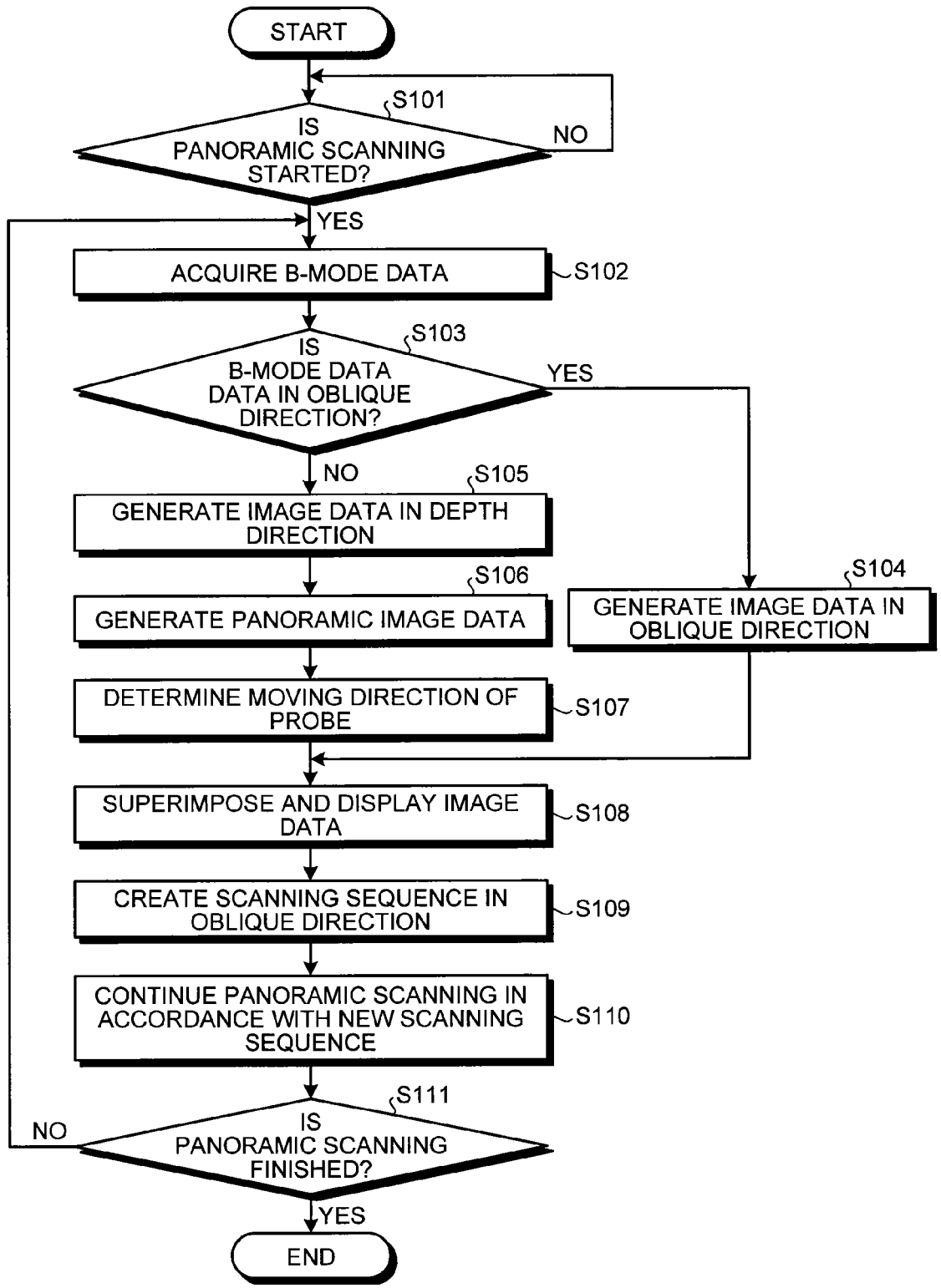
FIG. 10 is a flowchart of a process of panoramic scanning performed by the ultrasonic diagnostic apparatus according to the first embodiment.

FIG. 10 is a flowchart of a process of panoramic scanning performed by the ultrasonic diagnostic apparatus 100 according to the first embodiment. As illustrated in FIG. 10, if the scanning control unit 16c receives an instruction to start panoramic scanning from the operator, panoramic scanning is started (Yes at Step S101).

If the panoramic scanning is started, the image generating unit 14a acquires B-mode data from the B-mode processing unit 12 (Step S102). If the B-mode data thus acquired is data in an oblique direction acquired through second scanning (Yes at Step S103), the image generating unit 14a generates image data in an oblique direction (second image data) from the reflected wave data (Step S104).

By contrast, if the reflected wave data thus acquired is not data in an oblique direction acquired through the second scanning (No at Step S103), the image generating unit 14a generates image data in the depth direction (first image data) from the reflected wave data (Step S105). If the image generating unit 14a generates the image data in the depth direction, the image superimposing unit 14b superimposes overlapping portions of the image data thus generated and first image data generated previously, thereby generating panoramic image data (Step S106). The direction determining unit 16a determines the moving direction of the ultrasonic probe 1 (Step S107).

Subsequently, the display control unit 16d displays the panoramic image data and the image data in the oblique direction (second image data) in a superimposed manner on the display unit 2 (Step S108). The scanning control unit 16c newly creates a scanning sequence for performing the second scanning in a direction inclined toward the moving direction based on the moving direction determined by the direction determining unit 16a (Step S109). The scanning control unit 16c controls the transmitting and receiving unit 11 so as to continue the panoramic scanning in accordance with the scanning sequence thus newly generated (Step S110).

Subsequently, the scanning control unit 16c repeats the process described above until receiving an instruction to finish the panoramic scanning from the operator (No at Step S111). If the scanning control unit 16c receives an instruction to finish the panoramic scanning from the operator, the scanning control unit 16c finishes the panoramic scanning (Yes at Step S111).

As described above, according to the present embodiment, ultrasonic signals are transmitted and received in a direction inclined toward the moving direction of the ultrasonic probe with respect to the depth direction of the subject during scanning in panoramic scanning. Thus, second image data is acquired and displayed together with panoramic image data. As a result, it is possible to expand the field of view in the moving direction of the ultrasonic probe, thereby increasing the visibility in the moving direction of the ultrasonic probe during the scanning in the panoramic scanning.

Second Embodiment

A second embodiment will now be described. In the first embodiment, the explanation has been made of the example where the first image data and the second image data are two-dimensional image data. By contrast, in the second embodiment, an explanation will be made of the example where first image data and second image data are volume data, which is three-dimensional image data. In the second embodiment, three-dimensional panoramic data, which is three-dimensional panoramic image data, is generated from acquired volume data.

In the present embodiment, an ultrasonic probe 1 can acquire volume data, which is three-dimensional image data. The ultrasonic probe 1 is a 2D array probe or a mechanical 4D probe, for example.

In the present embodiment, a scanning control unit 16c controls a transmitting and receiving unit 11 so as to perform scanning for acquiring first volume data by transmitting and receiving ultrasonic signals in the depth direction of a subject as first scanning. The scanning control unit 16c also controls the transmitting and receiving unit 11 so as to perform second scanning for acquiring second volume data by transmitting and receiving ultrasonic signals in a direction inclined toward a moving direction with respect to the depth direction of the subject as the second scanning. Similarly to the first embodiment, the scanning control unit 16c controls the transmitting and receiving unit 11 so as to repeatedly perform the first scanning and the second scanning.

Similarly to the first embodiment, while the ultrasonic probe 1 is being moved, the scanning control unit 16c controls the transmitting and receiving unit 11 so as to stop scanning in a range positioned after a superimposing area in the moving direction of the ultrasonic probe 1 in a range that can be scanned by the ultrasonic probe 1 in the first scanning.

Figure 11:
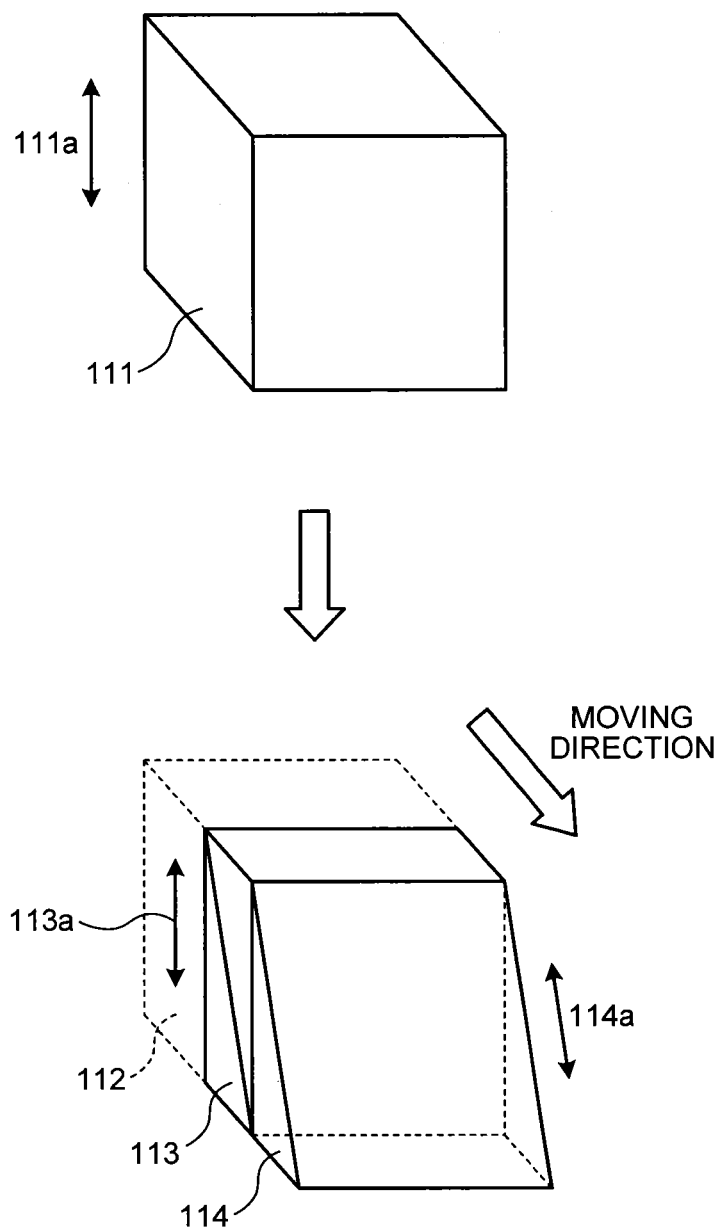
FIG. 11 is a view of scanning control performed by a scanning control unit according to a second embodiment.

FIG. 11 is a view of scanning control performed by the scanning control unit 16c according to the second embodiment. As illustrated in the upper figure of FIG. 11, when a direction determining unit 16a determines that the ultrasonic probe 1 is not being moved, the scanning control unit 16c performs scanning for transmitting and receiving ultrasonic signals in the depth direction of the subject (direction of an arrow 111a) on a range 111 that can be scanned by the ultrasonic probe 1. In the present embodiment, as illustrated in the upper figure of FIG. 11, the range 111 that can be scanned by the ultrasonic probe 1 is a three-dimensional area having predetermined widths in the depth direction of the subject and two directions orthogonal to the depth direction.

If the direction determining unit 16a determines the moving direction of the ultrasonic probe 1, the scanning control unit 16c controls the transmitting and receiving unit 11 so as to perform the first scanning for acquiring the first volume data by transmitting and receiving ultrasonic signals in the depth direction of the subject as illustrated in the lower figure of FIG. 11. At this time, the scanning control unit 16c controls the transmitting and receiving unit 11 so as to stop scanning in a range 112 positioned after the superimposing area in the moving direction of the ultrasonic probe 1 in the range 111 that can be scanned by the ultrasonic probe 1. In other words, the scanning control unit 16c controls the transmitting and receiving unit 11 so as to perform scanning in the depth direction of the subject (direction of an arrow 113a) only on a range 113 positioned before the range 112 in the moving direction of the ultrasonic probe 1 as the first scanning. Thus, similarly to the first embodiment, it is possible to eliminate unnecessary scanning while the three-dimensional panoramic scanning is being performed.

Furthermore, if the direction determining unit 16a determines the moving direction of the ultrasonic probe 1, the scanning control unit 16c controls the transmitting and receiving unit 11 so as to perform the second scanning for acquiring the second volume data by transmitting and receiving ultrasonic signals in a direction inclined toward the moving direction with respect to the depth direction of the subject as illustrated in the lower figure of FIG. 11. In other words, the scanning control unit 16c controls the transmitting and receiving unit 11 so as to perform scanning in the direction (direction of an arrow 114a) inclined toward the moving direction with respect to the depth direction of the subject on a range 114 expanded obliquely toward the moving direction with respect to the depth direction of the subject as the second scanning. In the present embodiment, as illustrated in the lower figure of FIG. 11, the range 114 is a triangular prism area having a base formed along the moving direction of the ultrasonic probe 1 and the depth direction of the subject. Thus, similarly to the first embodiment, it is possible to automatically expand the field of view in the moving direction correspondingly to the direction in which the ultrasonic probe 1 is moved by the operator. At this time, similarly to the first embodiment, the scanning control unit 16c may control the transmitting and receiving unit 11 such that the number of beams output in the second scanning is smaller than the number of beams output to the range in which the scanning is stopped in the first scanning while the ultrasonic probe 1 is being moved.

In the present embodiment, an image generating unit 14a generates volume data, which is three-dimensional image data, from three-dimensional B-mode data generated by a B-mode processing unit 12. Specifically, the image generating unit 14a performs coordinate conversion, data interpolation, or the like on the B-mode data generated by the B-mode processing unit 12, thereby generating the volume data. In the present embodiment, the image generating unit 14a generates the first volume data from three-dimensional B-mode data acquired through the first scanning and the second volume data from three-dimensional B-mode data acquired through the second scanning.

In the present embodiment, an image superimposing unit 14b generates three-dimensional panoramic image data by superimposing a plurality of pieces of first volume data acquired through the first scanning as a panoramic image. Specifically, every time first volume data is acquired, the image superimposing unit 14b superimposes a portion corresponding to the superimposing area set in a part of the range that can be scanned by the ultrasonic probe 1 in the first volume data thus acquired, with an overlapping portion in first volume data generated previously, thereby generating the three-dimensional panoramic image data. At this time, for example, the image superimposing unit 14b uses a typical pattern matching technology, such as the SAD method, to perform superimposing processing for superimposing the overlapping portions in the volume data.

Figure 12:
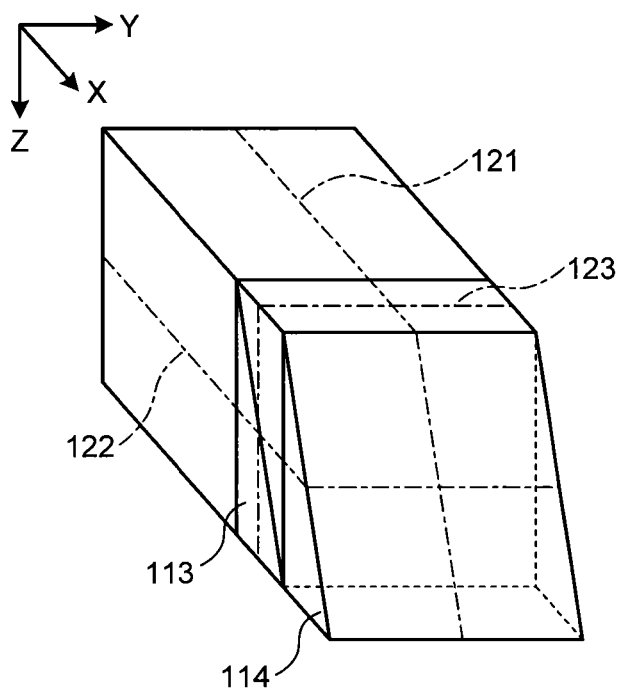
FIG. 12 is a view of three-dimensional panoramic image data generated by an image superimposing unit according to the second embodiment.

FIG. 12 is a view of three-dimensional panoramic image data generated by the image superimposing unit 14b according to the second embodiment. As illustrated in FIG. 12, for example, the image superimposing unit 14b uses only the first volume data acquired through the scanning of the range 113 among the range 113 and the range 114 illustrated in the lower figure of FIG. 11 for superimposing of the three-dimensional panoramic image data. Thus, as illustrated in FIG. 12, it is possible to obtain volume data of a wide area along the moving direction of the ultrasonic probe 1. The second volume data acquired through the scanning of the range 114 is not used for superimposing of the three-dimensional panoramic image data. The second volume data is displayed on a display unit 2 as information indicating the state in the travelling direction of the ultrasonic probe 1 by a display control unit 16d.

In the present embodiment, the display control unit 16d displays sectional image data along a predetermined direction in the second volume data together with sectional image data along the predetermined direction in the three-dimensional panoramic image data or in the first volume data on the display unit 2 during the scanning.

The display control unit 16d, for example, displays sectional image data along respective three orthogonal directions in the second volume data together with sectional image data along the respective three orthogonal directions in the three-dimensional panoramic image data or in the first volume data on the display unit 2 during the scanning.

Figure 13:
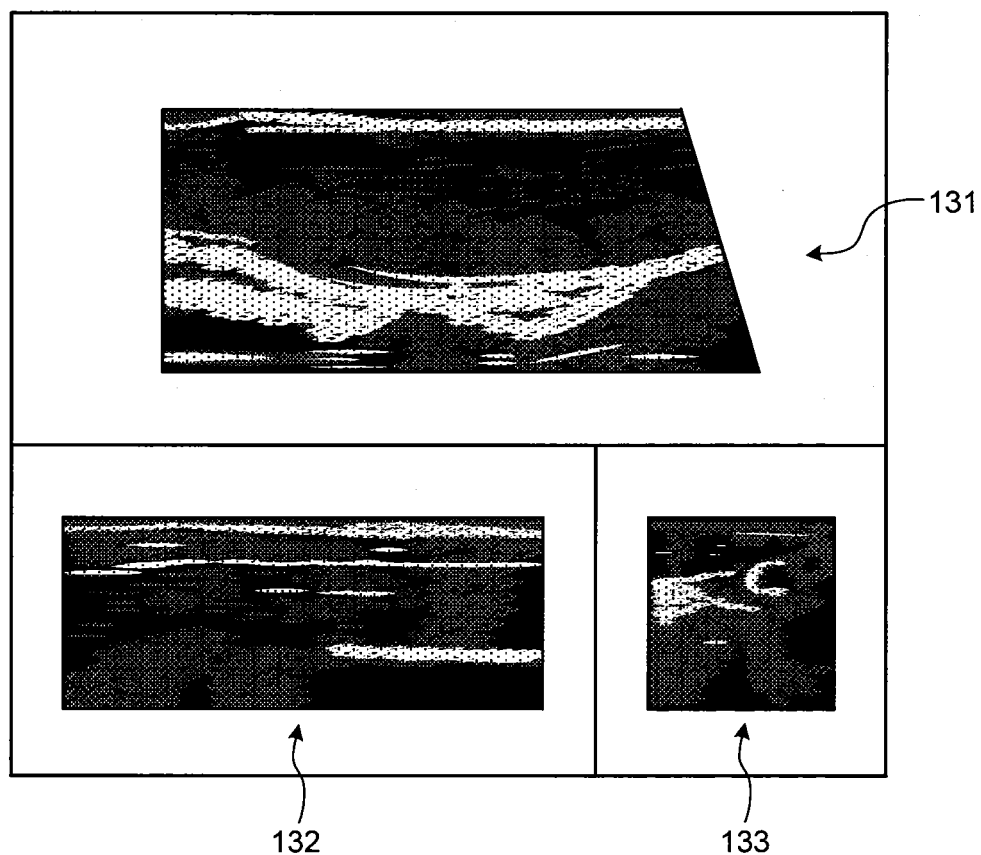
FIG. 13 is a view of an example of sectional image data displayed by a display control unit according to the second embodiment.

FIG. 13 is a view of an example of the sectional image data displayed by the display control unit 16d according to the second embodiment. While the panoramic scanning is being performed, for example, the display control unit 16d generates volume data by superimposing the three-dimensional panoramic image data generated by the image superimposing unit 14b and the second volume data generated by the image generating unit 14a. Subsequently, the display control unit 16d performs rendering processing with a multi-planer reconstruction (MPR) method on the volume data thus generated, thereby generating sectional image data along respective three orthogonal directions. The three orthogonal directions are three-axial directions in a three-dimensional coordinate system predefined for the scanning range of the ultrasonic probe 1, for example. Alternatively, the three orthogonal directions may be directions specified in advance by the operator. The display control unit 16d displays the three sectional image data thus generated on the display unit 2 while the panoramic scanning is being performed.

In the case where the ultrasonic probe 1 is a 2D array probe, for example, an assumption is made that one of the directions of two-dimensional array of transducer elements is defined as an X-axis direction, the other thereof is defined as a Y-axis direction, and the depth direction of the subject is defined as a Z-axis direction as illustrated in FIG. 12. In this case, for example, the display control unit 16d generates sectional image data of a section 121 parallel to the X-Z plane, a section 122 parallel to the X-Y plane, and a section 123 parallel to the Y-Z plane. The display control unit 16d then displays sectional image data 131 of the section 121, sectional image data 132 of the section 122, and sectional image data 133 of the section 123 on the display unit 2. As a result, if the ultrasonic probe 1 is moved in the X-axis direction, the range depicted in the image is expanded in the moving direction of the ultrasonic probe in the sectional image data 131 and 132. If the ultrasonic probe 1 is moved in the Y-axis direction, the range depicted in the image is expanded in the moving direction of the ultrasonic probe in the sectional image data 132 and 133.

The display control unit 16d, for example, may display sectional image data along the moving direction of the ultrasonic probe in the second volume data together with sectional image data along the moving direction of the ultrasonic probe in the three-dimensional panoramic image data or in the first volume data on the display unit 2 during the scanning.

In this case, the display control unit 16d acquires the moving direction of the ultrasonic probe 1 detected by the direction determining unit 16a while the panoramic scanning is being performed. Furthermore, the display control unit 16d generates volume data by superimposing the three-dimensional panoramic image data generated by the image superimposing unit 14b and the second volume data generated by the image generating unit 14a. Subsequently, the display control unit 16d performs rendering processing with the MPR method on the volume data thus generated, thereby generating sectional image data along the moving direction of the ultrasonic probe 1.

The display control unit 16d generates the sectional image data correspondingly to a change in the moving direction of the ultrasonic probe 1. The display control unit 16*d*, for example, acquires the moving direction of the ultrasonic probe 1 from the direction determining unit 16*a* at predetermined time intervals. Every time the display control unit 16*d* acquires the moving direction, the display control unit 16*d* generates volume data by superimposing the three-dimensional panoramic image data and the second volume data to generate sectional image data. The display control unit 16*d* displays the sectional image data thus generated on the display unit 2 while the panoramic scanning is being performed. As a result, even if the ultrasonic probe 1 is moved in an arbitrary direction, the range depicted in the sectional image data is expanded along the moving direction.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
    an ultrasonic probe configured to transmit and receive an ultrasonic signal to and from a subject;
    transmitting and receiving circuitry configured to drive the ultrasonic probe and scan the subject;
    processing circuitry configured to:
        determine a moving direction of the ultrasonic probe;
        control the transmitting and receiving circuitry to repeatedly perform a first scanning in a first direction and a second scanning in a second direction inclined toward the determined moving direction, wherein an oblique angle of the second direction is larger than an oblique angle of the first direction;
        generate a first image with respect to each first scanning;
        generate a second image with respect to each second scanning;
        generate a panoramic image by combining the first images from each first scanning;
        renew the panoramic image by using a newly generated first image without using the second images; and
        display only a newest one among the second images together with a newest panoramic image on a display during the first scanning and the second scanning.

2. The ultrasonic diagnostic apparatus according to claim 1, wherein
    the processing circuitry is configured to, every time the first image is generated, superimpose a portion corresponding to a superimposing area set in a part of a range capable of being scanned by the ultrasonic probe in the newly generated first image thus generated, with an overlapping portion in a first image generated previously, thereby renewing the panoramic image, and
    while the ultrasonic probe is being moved, control the transmitting and receiving circuitry so as to stop scanning in a range positioned forward of the superimposing area in the determined moving direction of the ultrasonic probe in the range capable of being scanned by the ultrasonic probe in the first scanning.

3. The ultrasonic diagnostic apparatus according to claim 2, wherein the processing circuitry is configured to, while the ultrasonic probe is being moved, control the transmitting and receiving circuitry such that number of beams output in the second scanning is smaller than number of beams output to the range in which scanning is stopped in the first scanning.

4. The ultrasonic diagnostic apparatus according to claim 1, wherein
    the processing circuitry is further configured to detect a velocity of movement of the ultrasonic probe, and
    control the transmitting and receiving circuitry so as to change the second direction depending on the detected velocity of movement of the ultrasonic probe.

5. The ultrasonic diagnostic apparatus according to claim 1, wherein the processing circuitry is configured to control a transmission delay time for each of a plurality of piezoelectric transducer elements included in the ultrasonic probe, thereby controlling inclinations of the first direction and the second direction.

6. The ultrasonic diagnostic apparatus according to claim 1, wherein
    the ultrasonic probe is configured to be capable of acquiring volume data that is three-dimensional image data,
    the processing circuitry is configured to:
        generate a three-dimensional first image with respect to each first scanning,
        generate a three-dimensional second image with respect to each second scanning,
        generate a three-dimensional panoramic image by combining the three-dimensional first images from each first scanning,
        renew the three-dimensional panoramic image by using a newly generated three-dimensional first image without using the three-dimensional second images, and
        display sectional image along a predetermined direction in a newest three-dimensional second image together with sectional image along the predetermined direction in a newest three-dimensional panoramic image or in a newest three-dimensional first image on the display during the first scanning and the second scanning.

7. The ultrasonic diagnostic apparatus according to claim 6, wherein the processing circuitry is configured to display sectional image along respective three orthogonal directions in the newest three-dimensional second image together with sectional image along the respective three orthogonal directions in the newest three-dimensional panoramic image or in the newest three-dimensional first image on the display during the first scanning and the second scanning.

8. The ultrasonic diagnostic apparatus according to claim 6, wherein the processing circuitry is configured to display sectional image along the determined moving direction of the ultrasonic probe in the newest three-dimensional second image together with sectional image along the determined moving direction of the ultrasonic probe in the newest three-dimensional panoramic image or in the newest three-dimensional first image on the display during the first scanning and the second scanning.

9. The ultrasonic diagnostic apparatus according to claim 1, wherein the processing circuitry is configured to display a newest first image with the newest one among the second images and the newest panoramic image on the display.

* * * * *